(12) United States Patent
Walmsley

(10) Patent No.: US 7,758,570 B2
(45) Date of Patent: Jul. 20, 2010

(54) LASER BEAM HOMOGENISERS IN MEDICAL APPLICATIONS

(75) Inventor: Richard Walmsley, South Yarra (AU)

(73) Assignee: Riancorp Pty Ltd, Henley Beach, South Australia (AU)

( * ) Notice: Subject to any disclaimer, the term of this patent is extended or adjusted under 35 U.S.C. 154(b) by 1107 days.

(21) Appl. No.: 10/519,181

(22) PCT Filed: Jun. 25, 2003

(86) PCT No.: PCT/AU03/00791

§ 371 (c)(1), (2), (4) Date: Oct. 6, 2005

(87) PCT Pub. No.: WO04/000420

PCT Pub. Date: Dec. 31, 2003

(65) Prior Publication Data

US 2006/0100676 A1 May 11, 2006

(30) Foreign Application Priority Data

Jun. 25, 2002 (AU) .................................. PS 3138

(51) Int. Cl.
*A61B 18/18* (2006.01)
(52) U.S. Cl. .................. 606/17; 606/13; 607/89
(58) Field of Classification Search ........... 607/89; 385/80; 606/9; 514/885; 219/121; 359/584, 359/599, 600

See application file for complete search history.

(56) References Cited

U.S. PATENT DOCUMENTS

| | | | |
|---|---|---|---|
| 4,547,037 A * | 10/1985 | Case | 359/15 |
| 5,068,515 A * | 11/1991 | van den Bergh et al. | 219/121.73 |
| 5,231,684 A * | 7/1993 | Narciso et al. | 385/80 |
| 5,509,917 A * | 4/1996 | Cecchetti et al. | 606/15 |
| 5,982,524 A * | 11/1999 | Fujimoto et al. | 359/208 |
| 6,033,431 A * | 3/2000 | Segal | 607/89 |
| 6,165,170 A * | 12/2000 | Wynne et al. | 606/9 |
| 7,184,614 B2 * | 2/2007 | Slatkine | 359/599 |

(Continued)

FOREIGN PATENT DOCUMENTS

SU  1561-062 A  4/1990

(Continued)

OTHER PUBLICATIONS

Physical Optics Corporation, Holographic Diffusers Can Efficiently and Cost Effectively Distribute Light, Dec. 2001, NIST, p. 2.*

(Continued)

*Primary Examiner*—David Shay
(74) *Attorney, Agent, or Firm*—Calfee, Halter & Griswold LLP

(57) ABSTRACT

A device is disclosed usable for low level laser therapy to induce a photochemical reaction (non-heating) which is used in the treatment of conditions like tendonitis and other soft tissue injuries, wound healing and pain relief. The arrangement proposed will allow the device to be a Class I laser device thus providing long term minimization of the running costs of the device. The device includes a laser generating means (10) for generating a laser beam (14), the laser generating means (10) having an apparent source size and homogenising means (12) for modifying the laser beam (14) for modifying the apparent source size of the laser beam (14).

15 Claims, 1 Drawing Sheet

U.S. PATENT DOCUMENTS 7,452,356 B2 * 11/2008 Grove et al. .................. 606/9
2004/0036975 A1 * 2/2004 Slatkine ..................... 359/584

FOREIGN PATENT DOCUMENTS

| SU | 1561062 A | * | 4/1990 | | |
|----|-----------|---|--------|---|---|
| WO | WO 95/18984 | | 7/1995 | | |
| WO | WO 9518984 A1 | * | 7/1995 | | |
| WO | WO 99/39410 A1 | | 8/1999 | | |
| WO | WO 02/56355 | | 1/2002 | | |
| WO | 2003/49633 | * | 6/2003 | .................. | 606/10 |

OTHER PUBLICATIONS

International Search Report from PCT/AU03/00791.

* cited by examiner

LASER BEAM HOMOGENISERS IN MEDICAL APPLICATIONS

FIELD OF THE INVENTION

This invention relates to laser systems and in particular to Lasers used in the medical field.

BACKGROUND OF THE INVENTION

Safety when using or being exposed to lasers is a very important consideration International Standards exist with regards to the classification of laser devices and the way in which different classes of laser can be used. Those laser devices that conform to the laser safety Class I definition (ie IEC825-1, AS2211) are considered the safest.

Laser emitting devices that do not fall within the Class I definition require the device and the user, and in medical applications the patient to use or be subject to one or more of the following: use of safety spectacles, interlock systems, warning lights, etc.

Laser emitting devices have a wide range of wavelength, energy and pulse characteristics and the classification system is a guide as to the way in which each device having one or more of those characteristics can be used and by whom the device can be used.

A Class I laser-emitting device can be used without restriction but in accordance with the manufacturer's instructions for the purpose for which it was designed. This means that special training and additional safety equipment is not required. Thus operating costs are less when compared to the attendant operating costs of other classes of laser-emitting devices.

A major consideration when designing laser-emitting devices is the amount of power that the source laser in the device is required to emit so as to provide adequate laser emission power from the laser device. One of the determinants of this characteristic is the required power density to be delivered at the application site over a desired area.

As the area required to be treated increases for a required power density so does the power of the source laser needed to support that requirement.

Apart from the power, pulse parameters and wavelength of the laser, another of the critical features in specifying the class of the laser is the apparent aperture of the laser source. The apparent aperture will determine the image size that the laser source can form for example on the retina of an inadvertent observer.

The requirement described above is sometimes referred to as the apparent source and it is this characteristic that is used to determine the class of the laser emitting device.

Current laser device configurations are restricted somewhat by the physics of the devices used to generate the source laser. For diode laser sources, the emitting aperture (the area of the spot beam) of the laser radiation is typically 7×1 microns for a 904 nanometer Gallium Arsenide (Ga—As) laser diode. These devices typically have pulsed outputs with 1 and 5 Watt peak powers with the pulse repetition and duration being variable to suit the application. There are many other laser diode configurations, the device type described above is an example of such devices.

In some applications it is desired to not only provide the laser radiation over a larger area but also to control the power density thus requiring an adequately high power laser source.

It is an aim of the invention described herein to provide a laser emitting device that meets not only a desired power density and spot area requirement, but that meets Class I requirements thus providing long term minimization of the running costs of the device.

SUMMARY OF THE INVENTION

Accordingly the present invention provides a device for a medical diagnostic or therapeutic purpose, said device including:
laser generating means for generating a laser beam, said laser generating means having an apparent source size;
homogenising means for modifying said laser beam;
wherein said modifying adjusts the apparent source size of said laser beam.

Preferably the homogenising means further modifies a spot size of said laser beam.

Preferably the apparent source size of said laser beam is greater than that required as a minimum condition for classification of said device as a Class I laser.

Preferably the homogenizing means includes an optical homogeniser.

Preferably the optical homogeniser includes a microlens array.

Optionally the optical homogeniser includes a holographic diffuser.

Preferably the device further includes positioning means for positioning said device at a predetermined distance and orientation from a surface according to a requirement of said medical purpose.

BRIEF DESCRIPTION OF THE FIGURES

Specific embodiments of the invention will now be described in some further detail with reference to and as illustrated in the accompanying figures. These embodiments are illustrative, and not meant to be restrictive of the scope of the invention. Suggestions and descriptions of other embodiments may be included within the scope of the invention but they may not be illustrated in the accompanying figures or alternatively features of the invention may be shown in the figures but not described in the specification.

DETAILED DESCRIPTION OF A PREFERRED EMBODIMENT

Although a particular medical application is described herein and a particular laser emitting device configuration is also described, it should be understood that these details are illustrative only and not meant to be limiting in any way upon the application or configuration of the principle of the invention.

In the medical field, low power level laser radiation is known to have beneficial medical effects in some disease and restorative therapies.

One example is the treatment of lymphoedema other examples include use of low level laser therapy to induce a photochemical reaction (non-heating) which is used in the treatment of conditions like tendonitis and other soft tissue injuries, wound healing and pain relief.

Clearly, the frequency, power level (continuously on or modulated on/off duty cycle of the radiation at the same or changing levels) and characteristics of the laser are determined by the nature of the treatment outcome desired by a clinician.

The area of effective laser irradiation on the relevant tissue or organ of the patient is a matter of design and specification by the clinician.

Laser source emitting 600-1000 nanometers wavelength at 1 mW to 1 W power can be used. Such devices are usually class IIIB but by using the invention described herein will become Class 1.

Figure 2:
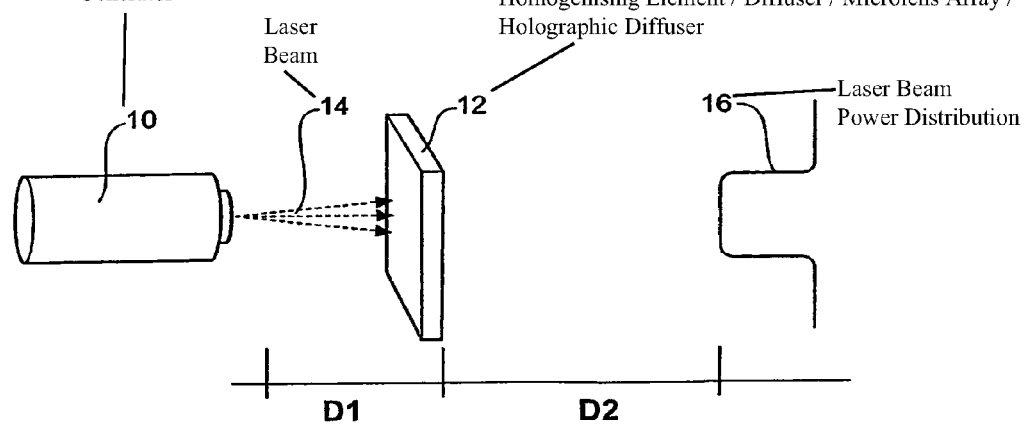
FIG. 2 depicts a generic arrangement of a preferred laser-emitting device according to the invention.

In a preferred arrangement the laser source is a Galium Arsenide Laser diode having an emitting aperture of 7×1 microns of 904 nanometer wavelength having 5-Watts peak power. In a lymphoedema application such as depicted in FIG. 2, the laser output is modulated or controlled to have a low 2,500 Hz and high 5,000 Hz repetition rate of 200-nanosecond duration. Such a device falls near the Class I and adjacent Class IIIB boundary.

Figure 1:
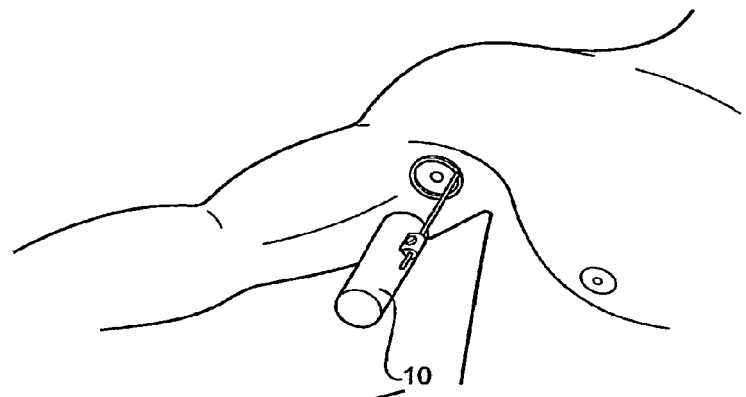
FIG. 1 depicts use of a preferred embodiment of the invention for the treatment of lymphodeama.

As shown in FIG. 1, in this type of medical procedure the operator holds the treatment device 20 incorporating the laser emitting device 10 so that the apparent aperture is moved in a predetermined path over the patient's treatment area. The treatment area is usually the tissue in near vicinity of the potentially or actually diseased lymph nodes, under the patients arm (as shown) or the groin area are examples of treatment sites. The treatment device 20 may include a plastic or metal frame 18 that has an abutment surface that is positioned on the treatment area to be irradiated whilst the other end is fixed relative to treatment device 20.

There is exists a slight divergence of the laser beam which is factored into the design, the amount of divergence being directly proportional to the distance between the output aperture of the laser diode and the patient's treatment site.

The invention includes the use of an optical homogeniser such as for example a CORNING™ high performance microlens array. A specification of its characteristics includes that it is made from either fused silica, silicon or polymer-on-silica. It has a center to center spacing tolerance of less than 1 micrometer and a total run-out over 50 mm of less than 7 micrometers. It has a maximum array size of 50 mm by 50 mm, a maximum substrate diameter of 150 mm and minimum substrate thickness of 400 micrometers.

Characteristics of the microlens are as follows. It can be spherical or aspherical and is designed with a polymer surface irregularity less than one quarter of a wavelength at 633 nanometers. For the silicon oxide ($SiO_2$) variety at least 97% of the lens surface has a surface irregularity of less than one half of a wavelength at 633 nanometers.

The focal length for a microlens can be designed to vary between 1.5 mm and 6.0 mm at wavelengths greater than or equal to 200 micrometers. The focal length tolerance in air for a polymer microlens is plus or minus 10 micrometers within the array and plus or minus 25 micrometers when measured array to array. For a $SiO_2$ array the focal length tolerance in air is plus or minus 50 micrometers within the array and plus or minus 50 micrometers when measured array to array.

Clear aperture dimension is less than or equal to 1.3 mm and surface roughness is less than 100 Angstroms A° (Ra). The operating temperature is permitted to be between 0 and 70° C.

The surface relief diffuser version of the microlens array is used in preferred arrangements that are designed to spread light in a predetermined gain distribution Both symmetric and asymmetric surface relief diffusers can be used dependent on the application. This is not the only type of homogeniser that can be used, there are other fabrication techniques such as holographic diffusers. The important aspect is that the homogeniser acts like a near perfect diffuser thus causing the apparent aperture to be the homogeniser not the aperture of the emitting device.

In the subject application the apparent aperture of the source laser device is made uniformly larger to the order of 6 $mm^2$.

The preferred distance between the laser source aperture and the optical homogeniser is 5 mm. This accounts for the divergence of the source laser beam and as a result the apparent aperture and power distribution is such that the full device falls well within Class I limits.

FIG. 2 displays the laser source 10 and a homogeniser element 12 located a distance D1 from the laser source. The slightly divergent laser beam 14 from the source is exaggerated for the purpose of illustration only. The resultant laser beam power distribution is pictorially shown at 16 a distance D2 from the homogeniser element.

Having the arrangement described allows for the power output of the source laser to be increased allowing the ideal required power distribution to be homogeneously distributed over a much greater area than would otherwise be the case. This in turn allows the total Laser-radiating device to remain within the Class I laser classification. This ultimately reduces cost to the patient.

A larger area can be treated at the same time, thus reducing treatment time and complexity of movement This further benefits the patient, as the period of potential discomfort is minimized.

It will be appreciated by those skilled in the art that the invention is not restricted in its use to the particular application described. Neither is the present invention restricted in its preferred embodiment with regard to the particular elements and/or features described or depicted herein. It will be appreciated that various modifications can be made without departing from the principles of the invention. Therefore, the invention should be understood to include all such modifications within its scope.

The invention claimed is:

1. A device for a medical diagnostic or therapeutic purpose, said device including:
    a laser generator generating a laser beam having an apparent source size; and
    a diffuser for adjusting the apparent source size of said laser beam, a laser safety classification of the laser being adjusted as a function of the apparent source size.
2. A device as claimed in claim 1 wherein the diffuser adjusts the apparent source size to about 6 $mm^2$.
3. A device as claimed in claim 1 wherein said diffuser is an homogeniser.
4. A device as claimed in claim 3 wherein:
    said homogeniser increases the apparent source size of said laser beam; and
    the laser safety classification of the laser is reduced as a function of the increased apparent source size.
5. A device for a medical diagnostic or therapeutic purpose, said device including:
    laser generating means for generating a laser beam, said laser generating means having an apparent source size;
    homogenising means for modifying said laser beam;
    wherein said modifying adjusts the apparent source size of said laser beam; and
    wherein a laser safety classification of the laser is modified as a function of the apparent source size.
6. A device as claimed in claim 5, wherein said homogenising means further modifies a spot size of said laser beam.
7. A device as claimed in claim 5, wherein said laser generating means includes a laser diode.

8. A device as claimed in claim 5, where said medical diagnostic or therapeutic purpose is the treatment of conditions ameliorated by photochemical low level laser therapy.

9. A device as claimed in claim 5 wherein said medical diagnostic or therapeutic process is the treatment of lymphodema.

10. A device as claimed in claim 5, wherein:
said modifying increases the apparent source size of said laser beam; and
the laser safety classification of the laser is reduced as a function of the increased apparent source size.

11. A device as claimed in claim 5, wherein said homogenizing means includes an optical homogeniser.

12. A device as claimed in claim 11, wherein said optical homogeniser includes a microlens array.

13. A device as claimed in claim 11, wherein said optical homogeniser includes a holographic diffuser.

14. A device as claimed in claim 5 further including a positioning means for positioning said device at a predetermined distance and orientation from a surface according to a requirement of said medical purpose.

15. A device as claimed in claim 14, wherein said positioning means includes a frame, said frame adjustably attached to said device and when in use for a medical diagnostic or therapeutic purpose providing an abutment surface relative to said treatment area.

* * * * *